United States Patent
Farin

(10) Patent No.: US 9,089,336 B2
(45) Date of Patent: Jul. 28, 2015

(54) MONOPOLAR RF-SURGICAL SNARES

(75) Inventor: Günter Farin, Tubingen (DE)

(73) Assignees: Endox Feinwerktechnik GmbH (DE); Günter Farin (DE)

( * ) Notice: Subject to any disclaimer, the term of this patent is extended or adjusted under 35 U.S.C. 154(b) by 603 days.

(21) Appl. No.: 13/360,199

(22) Filed: Jan. 27, 2012

(65) Prior Publication Data

US 2012/0172864 A1  Jul. 5, 2012

Related U.S. Application Data

(63) Continuation of application No. PCT/EP2010/060877, filed on Jul. 27, 2010.

(51) Int. Cl.
*A61B 18/18* (2006.01)
*A61B 18/14* (2006.01)
*A61B 17/00* (2006.01)
*A61B 18/00* (2006.01)

(52) U.S. Cl.
CPC ............. *A61B 18/14* (2013.01); *A61B 18/1492* (2013.01); *A61B 2017/00867* (2013.01); *A61B 2018/00083* (2013.01); *A61B 2018/00601* (2013.01); *A61B 2018/141* (2013.01); *A61B 2018/1407* (2013.01); *C08L 2201/12* (2013.01)

(58) Field of Classification Search
CPC .... A61B 18/18; A61B 18/14; A61B 18/1492; A61B 2018/141; A61B 2018/1407
USPC ...................................................... 606/27–50
See application file for complete search history.

(56) References Cited

U.S. PATENT DOCUMENTS

| | | | |
|---|---|---|---|
| 4,181,131 A | 1/1980 | Ogiu | |
| 4,718,419 A | 1/1988 | Okada | |
| 5,078,716 A * | 1/1992 | Doll | ................................ 606/47 |
| 7,571,729 B2 * | 8/2009 | Saadat et al. | ................... 128/898 |
| 7,789,881 B2 * | 9/2010 | Weitzner | ........................... 606/47 |
| 8,157,818 B2 * | 4/2012 | Gartner et al. | ................. 606/148 |
| 2009/0182324 A1 | 7/2009 | Kurtulus | |

FOREIGN PATENT DOCUMENTS

| | | |
|---|---|---|
| DE | 2808546 A1 | 8/1978 |
| DE | 3220940 A1 | 12/1983 |
| DE | 3626371 A1 | 2/1987 |
| DE | 19941105 A1 | 3/2001 |
| WO | 2005/079901 A1 | 9/2005 |

* cited by examiner

*Primary Examiner* — Scott Getzow
(74) *Attorney, Agent, or Firm* — Yakov Sidorin; Quarles & Brady LLP

(57) ABSTRACT

Symmetrical and asymmetrical snares are used for endoscopically controlled methods by which tumors in hollow organs of the gastrointestinal tract can be ensnared and RF-surgically removed from the organ wall for diagnostic and/or therapeutic purposes. These snares are characterized in that one of the two snare portions, in the case of asymmetrical snares the longer of the two snare portions, is completely electrically insulated or is made from electrically non-conductive material and that the other of the two snare portions is made from electrically conductive material and its surface is not electrically insulated. In one embodiment, the asymmetrical snare is characterized in that the long snare portion is so much flexurally stiffer than the short snare portion that it tensions the short snare portion like the string of a bow.

10 Claims, 3 Drawing Sheets

FIG. 3
FIG. 5
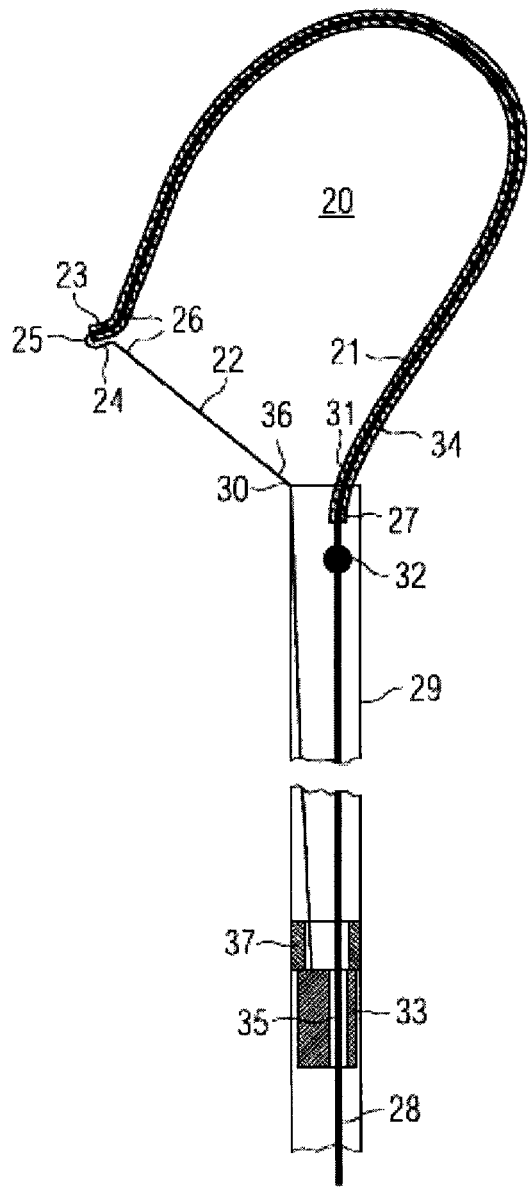
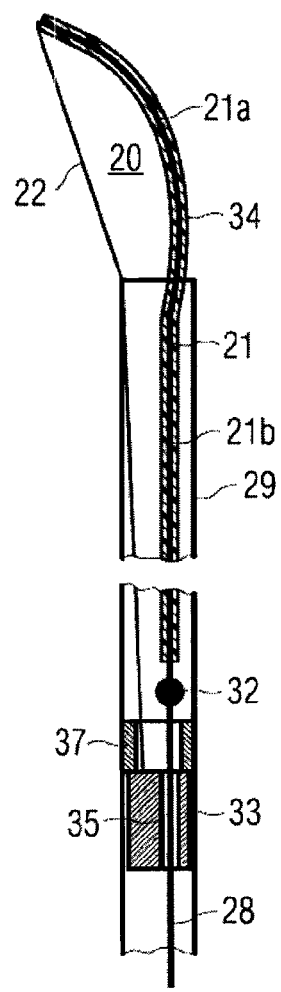

MONOPOLAR RF-SURGICAL SNARES

PRIORITY CLAIM

This application is a continuation of pending International Application No. PCT/EP2010/060877 filed on Jul. 27, 2010, which designates the United States and claims priority from German Patent Application No. 10 2009 036 158.8 filed on Jul. 28, 2009.

BACKGROUND OF THE INVENTION

1. Field of the Invention

The invention relates to radio-frequency-surgical (RF-surgical) snares for endoscopically monitored methods by which tissue in hollow organs, particularly pathological mucosal-submucosal areas or tumors of the gastrointestinal tract, can be ensnared and removed from the wall of the hollow organ by RF-surgical means for diagnostic and/or therapeutic purposes.

2. Description of Relevant Art

It is known that malignant tumors, also known as carcinomas, of the gastrointestinal tract, that is, the oesophagus, the stomach and the colon, cause metastases into other organs and are one of the four most common causes of death worldwide. 1 million new cases and 500,000 deaths are caused every year by malignant tumors of the colon alone, these tumors normally occurring in the mucosa or mucous membrane of the organ concerned through benign changes in the mucosa and then growing cancerously into the layers of tissue located under the mucosa, that is, into the submucosa and the muscularis propria or muscle layer as well as into the blood and lymph vessels located inside these. If a malignant tumor has grown into the blood or lymph vessels, malignant tumor cells may find their way through these vessels into other, and particularly vital, organs and there form metastases which cannot be easily treated or be treated at all. Since efferent blood and lymph vessels already start in the submucosa, earliest possible diagnosis and removal of malignant tumors of the mucosa are the surest means of preventing its proliferation in- and outside the organ wall concerned and/or metastasising into other organs.

If during an endoscopic examination of the gastrointestinal tract pathologically remarkable mucosal areas are found, a diagnostic examination of this mucosal area for carcinomatous components and their proliferation into the submucosa containing the blood and lymph vessels is indicated. For this the mucosal area concerned with the submucosa underneath it must as far as possible be separated from the organ wall en bloc, that is, in one piece and completely, that is, in depth as close as possible to the muscularis propria and planarly at sufficient distance from the pathologically remarkable mucosal area, and removed from the gastrointestinal tract for pathohistological examination. Here it should be noted that the wall of the hollow organs of the gastrointestinal tract, and particularly that of the colon, is at approx. 2 mm very thin, and particularly that the normal mucosa of the colon is only approx. 0.3 mm thick and the normal submucosa located underneath it only approx. 0.3 mm to 0.7 mm thick, while the planar extension of a pathologically remarka ble mucosal area may be several centimeters in diameter.

Pathological mucosal-submucosal areas may in their demand for space spread into the lumen of hollow organs, that is, project from the level of the surface of the normal mucosa, and form what are known as polyps. Pathological mucosal-submucosal areas may however also occur planarly and without projecting from the level of the normal mucosa.

Known methods of separating and removing pathological mucosal-submucosal areas or tumors in the gastrointestinal tract are in particular endoscopic polypectomy (EPE), endoscopic mucosa resection (EMR) and endoscopic submucosal dissection (ESD).

These methods all have the common purpose of completely removing tumors for diagnostic or therapeutic purposes. This purpose is achieved when the pathohistological examination of the removed tissue confirms fulfilment of the criteria of an RO resection according to the UICC classification, i.e. that the EPE, EMR or ESD has removed the whole of the pathological, particularly the malignant, tumor tissue, or that it has been performed in the healthy tissue outside the pathological, particularly the malignant, tumor. With regard to a pathohistological examination of the removed tissue and the spatial assignment of a particularly malignant result in the removed tissue to the respective ectomy, resection or dissection limit on the organ concerned removal in toto and en bloc, that is, totally and in a single piece, is advised and particularly in the case of large or large-area tumors even essential for a safe pathohistological examination and evaluation of the removed tissue with regard to the radicality of the removal of benign and in particular malignant tissue.

By endoscopic polypectomy (EPE) is generally meant a method where a loopshaped RF surgical electrode, known generally as a polypectomy snare, is looped around a polyp to be removed and RF-surgically ectomised or separated in toto and en bloc from the organ concerned or the organ wall. RO polypectomy in toto and en bloc is possible only if a polypectomy snare is placed securely around the base or near to the muscularis propria of the organ wall concerned underneath the polyp to be ectomised and the polyp can be ectomised RF-surgically in toto and en bloc close to the muscularis propria. If a pathological mucosal-submucosal area projects too little or not at all above the normal mucosal-submucosal area, it cannot be securely ensnared or ensnared at all with a polypectomy snare and cannot be ectomised. In such a case one injects, for example, physiological NaCl solution into the submucosa underneath the mucosal area or tumor concerned in order to raise the mucosal-submucosal area concerned far enough above the level of the normal mucosa-submucosa level for a polypectomy snare to be placed around it and for it to be resected RF-surgically as close as possible to the muscularis propria of the organ wall located underneath it. This method is, as already mentioned above, accordingly known as endoscopic mucosal resection (EMR).

Known instruments for EPE and EMR incorporate essentially an RF-surgical snare, a flexible catheter, one or more flexible manipulation wires which extend inside the catheter in an axial direction for pulling out or inserting the snare from or into the distal end of the catheter and to conduct the RF-current needed for RF-surgical removal of the tissue round which the snare is looped and a handle at the proximal end of the catheter, which catheter consists of a slide rail and a sliding member for manually pushing out or pulling in the snares from or into the distal end of the catheter. Disposed on the sliding member is at least one electrical contact for connection to an RF-surgical generator (RF generator). By polypectomy snare is generally meant pars pro toto the whole instrument, including a polypectomy snare integrated into it, and specifically a separate polypectomy snare separate from the instrument. For the sake of clarity, the separate polypectomy snare will in the following be referred to as "snare" for short and the whole instrument, including the snare, as "instrument." Instruments with a fixedly integrated snare should to avoid hygiene problems and in the absence of adequate cleansing and disinfection facilities be used only once or on the same patient. Instruments with exchangeable snare can be adequately cleaned and disinfected and may therefore be used a number of times or on different patients. This invention accordingly relates both to separate snares and to instruments with an integrated snare.

As regards the technique for applying the snare a distinction is made between symmetrical snares or snares that open and close symmetrically and asymmetrical snares or snares that open and close asymmetrically. For a description of the differences between symmetrical and asymmetrical snares it is practical to consider snares consisting of two snare portions which are connected together to form a loop at their proximal and distal ends.

Monopolar symmetrical snares incorporate two snare portions which are of equal length and which are connected at their proximal ends to the distal end of a manipulation wire and therefore are or can be pushed out of or pulled into the distal end of the catheter at the same time and at the same speed. Consequently the two snare portions must be of the same length, regardless of whether the two snare portions connected together are mirror-image identical or differently shaped or preshaped.

Monopolar asymmetrical snares incorporate two snare portions, one longer than the other. Only the proximal end of the longer of the two snare portions is connected to the distal end of a manipulation wire and can thus be actively pushed out of or pulled into the distal end of the catheter. The shorter snare portion which is mechanically connected at its distal end to the longer snare portion at its distal end can be passively pulled out by the longer snare portion from the distal end of the catheter as far as a stop which is disposed on a stop device disposed at the distal end of the catheter and which acts at the proximal end of the shorter snare portion. Known stop devices are combined with a driving device. Here the longer snare portion is fitted with a mechanical driver which, when the longer snare portion is pulled back from a defined position, also pulls the shorter snare portion into the distal end of the catheter at the same time. This combined stop-driver device is on known asymmetrical polypectomy snares disposed direct at the distal end of the catheter.

Since the introduction of EPE and EMR there has been a wish to remove increasingly large polyps or pathological mucosal-submucosal areas of the gastrointestinal tract for diagnostic and/or therapeutic purposes, and this with a view to pathohistological examination, as already mentioned above, as far as possible in toto and en bloc. However, as the size of the polyps ectomised or mucosal-submucosal areas resected in toto and en bloc has increased, the resulting problems and complications set out below have increased with the use of the snares available hitherto for EPE and EMR and the RF generators available for operating these snares.

One of these problems consists in the fact that particularly with en-bloc separation of large polyps or large-area mucosal-submucosal areas, particularly if through submucosal injection these become even greater than they are already before injection, is the electrical power required for this. Since the RF-surgical cutting effect can then and only then be achieved if between the snare used for cutting and the tissue to be cut electric arcs which burn away the tissue located close to the polypectomy or mucosectomy snare (pyrolysis) occur at sufficiently high RF voltage, the tissue close to the snare must be heated to the boiling temperature of water beforehand so that between the snare and the tissue an electrically insulating layer of water vapour is created in which at sufficient electrical field strength electric arcing then occurs. If this tissue is heated too slowly or with too long a time lag, which it is feared may result in a delay in initial incision, the heat created here may diffuse from the tissue into the adjacent tissue close to the snare and damage the adjacent tissue thermally. If for the abovementioned reason the snare is applied close to the organ wall, the muscularis propria may be thermally damaged by it. Thermal damage to the muscularis propria or even the serosa of a hollow organ of the gastrointestinal tract may result in perforation of this organ and will not infrequently make an open surgical operation necessary.

For a sufficiently lag free initial incision during polypectomy or mucosaresection an RF current of approx. 0.5 amperes per cm of snare length is required. Since RF generators of known RF surgical instruments generate 1.5 to 3 amperes at maximum, only polyps or mucosal-submucosal areas with a maximum diameter in the application area of the snare of approx. 1 to 2 cm—corresponding to an effective snare length of approx. 3 to 6 cm—can be separated en bloc with a sufficiently short initial-incision lag. With larger polyps or mucosal-submucosal areas there is actually no cutting effect at all.

To solve this problem it is disclosed by G. Maslanka in the German patent application publication DE 100 28 413 A1, that the snare, there referred to as "electrode", or the snare wire, there referred to as the "electrode core", be lined with an insulating sheath. Here the free electrode surface of the electrode core is in one or more parts of the electrode reduced by a portion of the insulating sheath incorporating a large number of holes. Alternatively the effective electrode surface of the snare electrode can be limited to an area near the electrode tip by insulation-sheathing of the two snare portions. This last was disclosed as early as 1975 by Karl Storz in the German patent application publication DE 2514501 and 1990 by L. F. Doll in U.S. Pat. No. 5,078,716.

The snare as disclosed in DE 2514501 is a bipolar snare comprising two mirror-image-formed snare halves, referred to there as "electrodes." Here the two electrodes form a snare in that they are connected together at their ends by means of an insulating element and in that the electrodes are provided with an insulating layer along their entire length, with the exception of an area close to the insulating element.

Bipolar snares have, however, not proved satisfactory in clinical applications. One reason for this is the electrically insulating segments at the proximal and/or at the distal end between the two snare portions. For RF-surgical incisions the amplitude of the RF voltage must reach at least 200 volts between an active electrode used for incisions and the tissue to be cut. Since with bipolar instruments 200 volts with opposing polarity or phasing must be reached on each of the two active electrodes at the same time, the electrical insulation segments between the two active electrodes must, particularly at the proximal or distal end of the snare, where the distances between the two electrodes are very short, withstand a voltage amplitude or amplitude difference of at least 400 V. If electric arcing occurs between the two electrodes at these points, these electrodes may melt because of the high temperature of this electric arcing. For this reason bipolar snares have not proved satisfactory in practice.

In the U.S. Pat. No. 5,078,716 titled "Electrosurgical Apparatus for Resecting Abnormal Protruding Growth" a monopolar polypectomy snare is described by example of FIG. 1, the two snare portions of which are proximally with the exception of relatively short segments at the distal end of the snare electrically insulated so that only a relatively short segment at the distal end of the snare is insulated and is thereby RF-surgically effective. Although snares of this kind require less RF current during the initial-incision phase and during the incision phase than snares of the same size without insulation, they have the disadvantage that the RF-surgically effective part of the snare viewed from an endoscope is always behind the polyp, that is, is out of sight, and there is a risk that the distal tip of the snare can perforate the organ wall unmonitored. Avoiding the latter is, amongst other things, the subject of DE 100 28 413 A1. Here the active electrode surface is reduced by sheathing with holes in it. This form of electrode may, however, hinder accurate incision.

Both with electrosurgical instruments in accordance with U.S. Pat. No. 5,078,716 and DE 100 28 413 A1 and coagulating instruments in accordance with DE 25 14 501 the RF-surgically effective electrode surfaces can be disposed only at the distal end of the snare, with the disadvantage that these, seen through an endoscope, are always behind the tissue to be removed and the incision therefore has to be made without visual monitoring, which is a risky process, particularly with large polyps or mucosal-submucosal areas.

A further problem is the placing of the snare around in particular large or oddly shaped polyps or around polyps or mucosal-submucosal areas which have become enlarged through the injection of physiological NaCl solution or other injectables into the submucosa, that is, by submucosal injection, enlarged or oddly shaped polyps or mucosal-submucosal areas. To solve this problem special snare shapes, for example, hexagonal or crescent-shaped snares, and designs, and particularly asymmetrical snares or rotatably symmetrical snares, have been and are being developed, with which these polyps or mucosal-submucosal areas can also be ensnared. However, all these snares for separating the tumor close to the muscularis propria must for the above-mentioned reason not be pressed against the organ wall during RF-surgical incision.

A further problem is the placing and guidance of the snare as close to the organ wall as possible in order to separate the tumor close to the muscularis propria for the above-mentioned reasons. With multi-strand or braided standard snares this is normally not practicable, because these snares are too soft or too flexible for this. To overcome this problem special snares are recommended, such as monofilament snares or flat snares which are so flexurally stiff that they can be pressed firmly against the organ wall or into the mucosa. The use of these snares is, however, hazardous in so far as because of the pressure against the organ wall they can also cut into or even through the organ wall.

A further problem, particularly with large polyps or mucosal-submucosal areas with an abnormally slippery surface may be that the snare slips out of the intended position while being applied or manipulated. Since wide open snares, especially when being placed around flat polyps or mucosal-submucosal areas, cannot or must not be pressed against the organ wall concerned sufficiently firmly, they may, when the snare is closed, slip over the slippery mucous membrane and out of the intended position.

To avoid this problem polypectomy snares are known which are fitted with little claws or spurs or in which the snare wire is folded at a number of points to form small claws or spurs which, when the snare is closed, hook into or grip the tissue to prevent slipping. However, these claws or teeth must not be too long or too large, as otherwise they may prevent the snare from being pulled back into the only approx. 1 mm-wide hole at the distal end of the catheter. On asymmetrical snares claws, hooks or teeth of this kind interfere with the function of the above-described driving device.

Although endoscopic polypectomy and endoscopic mucosaresection are regarded today as clinically established methods, these methods are presumably also because of the above-described problems attended with various complications.

Complications in this regard are in particular bleeding from injured blood vessels, perforation of the organ wall and relapses as a result of incomplete removal of a tumor. The rate of these complications rises, amongst other things, in proportion to the size of the tumor removed (T. Rösch: Endoskopische Mukosaresektion im oberen und unteren Gastrointestinal-Trakt. Dtsch Med Wochenschrift 2004; 129: 126-129 MUPS). Both because of the above-described problems and because of the complication rate rising due to the mean diameter of the tumor the hitherto available abovementioned methods and snares only can only be used to remove polyps or mucosal-submucosal areas in toto and en bloc with a maximum mean diameter of up to approx. 2 cm. With these methods larger polyps or mucosal-submucosal areas can be removed only by a piecemeal technique and often not radically or completely, a circumstance which may result in relapses.

In order to remove in toto or en bloc as closely as possible to the muscularis propria of organ walls large mucosal-submucosal areas which cannot be removed in toto and en bloc safely or at all with available snares and RF generators various endoscopic submucosal dissection (ESD) methods have been and are being developed and some are already being applied clinically. A common feature of these methods is the RF-surgical removal of the mucosal-submucosal area from the organ wall as closely as possible to the muscularis propria with, for example, a needle electrode.

These methods, however, call for a high degree of manual dexterity, experience, constant training, a willingness to take risks and long operating times. So far there have been only a very few experts who practise these methods.

SUMMARY OF THE INVENTION

The embodiments are based on the object of improving monopolar symmetrical and monopolar asymmetrical polypectomy snares and RF-surgical snares for the endoscopically monitored separation of pathological tissue, particularly tumors of the mucosa and or submucosa of organ walls of the gastrointestinal tract in the application of which the above-stated problems and/or complications arise less or do not arise at all.

The object of the invention is particularly to develop RF-surgical snares with which even large tumors of this kind which have hitherto had to be removed by the piecemeal technique, endoscopic mucosa dissection (ESD) or even open surgery can be RF-surgically removed in toto and en bloc from organ walls of the gastrointestinal tract.

It is also the object of this invention to design these snares so that they can be pressed against the wall of a hollow organ before and particularly also during RF-surgical incision without cutting RF-surgically into the wall.

A first embodiment relates to a monopolar snare with which tissue to be removed can be ensnared and RF-surgically removed. The snare may be both a symmetrical and asymmetrical snare. It includes two snare portions each of which incorporates a proximal and a distal end. At least one snare portion is connected at the proximal end to a manipulation wire which can be moved inside a catheter or can at least be connected to this manipulation wire. By means of the manipulation wire the at least one snare portion can be pulled into or pushed out of the catheter. The two snare portions are connected together at their distal ends or are made in a single piece. Furthermore, one of the two snare portions is able to conduct electricity in such a way that current can flow from an RF surgical generator into the tissue with which this snare portion is in contact. The other of the two snare portions is electrically insulated along its entire length in such a way that no current can flow from an RF surgical generator into the tissue with which the snare portion is in contact. It is preferable if the insulated snare portion is connected to the manipulation wire.

It is especially advantageous if the electrical insulation is provided at the surface of the insulated snare portion and/or at the distal and/or proximal end of the snare portion. The insulated snare portion can, however, also be made from an insulating material.

Alternatively, the insulation can be provided on and/or in the catheter and/or on the manipulation wire and/or at least one points of connection to the insulated snare portion. Preferably the insulation should be between the manipulation wire and the insulated snare portion. In these cases the insulated snare portion may also be made from electrically conductive material. By combining a number of insulations the overall insulation can be improved.

Preferably at least one of the snare portions incorporates or incorporate a wire, for example, a metallic round wire and/or flat wire and/or a stranded wire.

Preferably at least one of the snare portions incorporates or incorporate a resilient material.

It is advantageous if the two snare portions form together at their distal ends a resilient bending element and/or hinge, which enables the snare to be opened and shut repeatedly and resiliently.

Preferably the two snare portions are connected to each other mechanically or electrically or only mechanically at their distal ends by a connecting element which is optionally electrically conductive or insulating.

A snare according to an embodiment can be constructed as a symmetrical snare. On symmetrical snares of this kind, i.e. snares on which the two snare portions are more or less of the same length, it does not matter which of the two snare portions is electrically insulated or is made from electrically non-conductive material or which of the two snare portions is made from electrically conductive material and is not electrically insulated.

The advantage of a snare according to the invention compared with known symmetrical snares not only consists in the fact that they require only 50% of the electric power of corresponding or electrically uninsulated symmetrical snares so that with it tumors of approximately twice the size can be removed en bloc from the wall of a hollow organ but also that the electrically uninsulated or RF-surgically active snare portion can be at least partly seen through an endoscope. Since the thermal effects caused by RF current normally occur simultaneously and largely identically along the length of the entire RF-surgically active snare portion, it is already an advantage that at least the part of this snare portion which can be viewed through an endoscope can be observed.

On known symmetrical snares on which both snare portions are electrically insulated at their proximal ends, such as suggested in DE 10028413 A1 by FIGS. 14 to 17 or in U.S. Pat. No. 5,078,716 by FIG. 1, it cannot be seen whether and if not why the intended RF-surgical effect does not occur or even whether unintended RF-surgical effects occur which might, for example, cause damage to the organ wall, the latter, for example, as the result of too long an initial-incision lag.

A snare in accordance with the invention may be in particular an asymmetrical snare on which the two snare portions are of different lengths so that a short snare portion is shorter than a long snare portion. On this snare the long snare portion is electrically insulated and connected to the manipulation wire at its proximal end.

This asymmetrical snare has a number of advantages over known asymmetrical snares.

One advantage consists in the fact that it requires less than 50% of the electric power of corresponding but electrically uninsulated asymmetrical snares. If the short, electrically uninsulated or RF-surgically active snare portion is, for example, 2 cm long and the long, electrically insulated or RF-surgically inactive snare portion is, for example, 10 cm long, this asymmetrical snare needs only approx. 20% of the electric power of a comparable electrically uninsulated snare.

A further advantage with an asymmetrical snare of this kind consists in the fact that the short or RF-surgically active snare portion can be almost completely seen through an endoscope.

A further advantage with this asymmetrical snare consists in the fact that the short or RF-surgically active snare portion is always of the same length, regardless of the size of the tissue or tumor to be separated, given, of course, that the minimum size is at least twice as long as the length of the short snare portion. Accordingly, even with en bloc removals of very large tumors there are no problems with the application of this asymmetrical snare as regards insufficient electrical conduction, particularly no dangerous initial-incision lags and consequently possible damage to an organ wall of the gastrointestinal tract. As a result even large tumors of the mucosa can be massively injected submucosally and then be RF-surgically removed en bloc close to the muscularis propria.

A further advantage of this asymmetrical snare consists in the fact that thanks to the length of the short or RF-surgically active snare portion remaining unchanged during the entire incision phase the cutting quality (ceteris paribus) is largely independent of the total length of the snare located outside the distal end of the catheter.

A further advantage with this asymmetrical snare consists in the fact that the cutting quality (ceteris paribus) can be repeated from case to case and everywhere.

A further advantage with this asymmetrical snare consists in the fact that the long or RF-surgically inactive snare portion may touch the organ wall even during the RF-surgical phase without having to fear that the organ wall will hereby be thermally damaged. This advantage is particularly relevant during removal of flat tumors, if the mucosa is cut open during the placing of the snare around the tumor in the manner of circumcision so that a groove is produced around the tumor into which the snare is inserted close to the muscularis propria and consequently gains sufficient grip. Here it is very important that the muscularis propria does not get thermally damaged.

A further advantage with this asymmetrical snare consists in the fact that on the long or RF-surgically inactive snare portion no electric arcing occurs and consequently this mechanically important snare portion is not negatively in its mechanical properties.

The short snare portion of an asymmetrical snare can by means of the long snare portion be passively pulled out of the catheter as far as the stop on a stop device disposed in the catheter and pulled into the catheter by means of a driver which is disposed on a stop device disposed at the proximal end of the short snare portion and which is disposed on the long snare section or on the manipulation wire.

Preferably the stop device and the driver inside the catheter are disposed so as to be displaced at least so far in a proximal direction that the driver remains inside the distal end of the catheter even when the long snare portion has been completely pushed out.

An advantageous further development of the asymmetrical snare is characterised in that the long or RF-surgically inactive snare portion is flexurally stiffer than the short or RF-surgically active snare portion. It is preferable that because of the long flexurally stiffer snare portion the short snare portion between the distal end of the catheter and the distal end of the long flexurally stiffer snare portion is tensioned like the string of a bow. The different flexural stiffness can be achieved, for example, by means of appropriate material properties, wire diameters and/or even by shape design. Because of the greater flexural stiffness the snare can be better pressed against the tissue and opened further than with conventional snares on which the two snare portions are made from the same material. Accordingly, with flexurally stiffer material the area enclosed by the snare can be greater. Furthermore, here the snare emerges from the catheter virtually axially so that the entire snare is opened out almost laterally to the axis of the catheter.

One advantage of this further development of the asymmetrical snare consists in the fact that this snare can open wider and also retains its shape when it is opened wide.

A further advantageous further development of this asymmetrical snare is characterised in that the long or RF-surgically inactive snare portion and a manipulation wire connected to it at its proximal end are rotationally or torsionally rigid and that the short or RF-surgically active snare portion is preferably rotationally or torsionally flexible. Preferably rotations of the manipulation wire are thereby at its proximal end transmitted to the snare as directly as possible and largely proportionally. The different rotational or torsional rigidity can be achieved by means of appropriate material properties and/or wire diameters.

The electrically insulated snare portion is preferably made from the same material as the manipulation wire, for example, in that the long snare portion is an extension of the manipulation wire.

One advantageous embodiment of this further development is characterised in that the long or RF-surgically inactive snare portion and/or the manipulation wire is or are made from NITINOL.

One decisive advantage of the two above-mentioned further developments consists in the fact that this asymmetrical snare can even during RF-surgical incision be pressed laterally to the axial direction of the catheter and/or by rotation or rotational swivelling of the snare against the organ wall under control and firmly. With this asymmetrical snare tumors of any size the removal of which has hitherto been possible only by the piecemeal technique or considerably more complicated submucosal dissection (ESD) can be removed en bloc close to the muscularis propria.

A further embodiment of the asymmetrical snare is characterised in that particularly the distal end of the long snare portion is preshaped such that this distal end already describes a small curve before the short snare portion is pulled out of the catheter as far as its stop. By this embodiment the force required to push out the long snare portion is reduced, particularly at the point where the short snare portion is pulled out of the catheter as far as its stop and from where further pushing out of the long snare portion is intended to tension the short snare portion like the string of a bow. Furthermore, with this embodiment, when the snare is tightened, the long snare section is not pushed into the catheter by the tension of the short snare portion unmonitored. The phenomena which can be avoided by preshaping the distal portion of the long snare portion are caused when the long snare portion is pushed out of the catheter and when the snare is tightened by the vectoral direction of the forces effective here. These phenomena are the more pronounced the flexurally stiffer the long snare portion is.

One advantageous embodiment of this further development is characterised in that the surface of the long or RF-surgical inactive snare portion is provided with a mark which enables both the longitudinal forward and backwards movement and the counterclockwise and clockwise rotation of the long snare portion to be visually monitored. This mark can be characterised, for example, in that a spiral strip with a colour contrasting with the surface of the long snare portion can be wrapped around the long snare portion.

One advantageous embodiment of particularly the asymmetrical snare relates to the design of the surface of the electrically insulated snare portion which is textured in such a way that the snare cannot easily or simply cannot slip off slippery tissue. Preferably the texture is disposed facing the centre of the snare or around the inside diameter of the snare portion.

Preferably the surface of the electrically insulated snare portion is coated with small sharp and/or pointed granular material of the kind normally applied to glass- or sandpaper.

The surface of the electrically insulated snare portion can advantageously also incorporate at least one projecting portion, which may be a burr, which, on the one hand, hinders or even prevents the snare from slipping sideways off slippery mucosa and, on the other, also does not or do not hinder the long snare portion from sliding longitudinally on non-slippery mucosa while the snare is tightening before and during incision.

This at least one projecting portion can advantageously be an integral constituent of an electrical insulation layer on the insulated snare portion.

One advantage of this embodiment consists in the fact that the snare does not slip out of the intended position when being placed around a slippery tumor but with non-slippery tumors can also slide as unobstructedly as possible over the mucosa in a longitudinal direction.

A further aspect of the invention is a monopolar snare with which tissue to be removed can be ensnared and removed RF-surgically. The surface, preferably the part of the surface directed towards the center of the snare, incorporates at least one projecting portion which, on the one hand, hinders or hinder or even prevents or prevent the snare from slipping sideways off the tissue to be removed and, on the other, does not hinder or even prevent the snare from sliding longitudinally when the snare is being tightened before and during the incision.

Another aspect of the invention relates to an RF-surgical instrument with a monopolar snare in accordance with the invention. The instrument has a catheter with a distal and a proximal end, a handle for monopolar symmetrical and/or asymmetrical snares at the proximal end of the catheter, a monopolar snare and at least one manipulation wire inside the catheter between the handle and the snare to manipulate the snare and conduct RF current to the snare.

BRIEF DESCRIPTION OF THE DRAWINGS

In the following, the invention will be described by way of example, without limitation of the general inventive concept, on examples of embodiment and with reference to the drawings.

FIG. 3 shows an exemplary embodiment of a monopolar asymmetrically opening and closing polypectomy snare.

FIG. 5 shows a preshaped curve in the distal area of the long snare portion.

Figure 1:
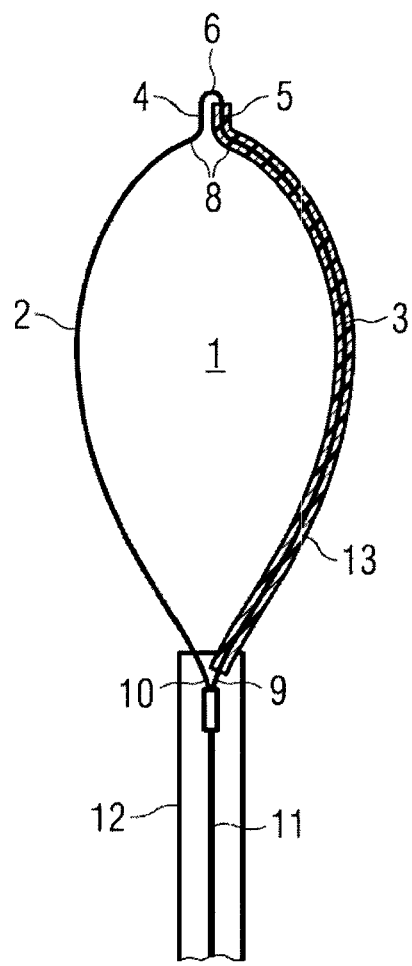
FIG. 1 shows a an exemplary embodiment of a monopolar symmetrically opening and closing polypectomy snare.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

FIG. 1 shows an exemplary embodiment of a monopolar symmetrically opening and closing polypectomy snare, with which tissue to be removed can be ensnared and RF-surgically removed. This snare includes two snare portions 2, 3 essentially of equal length made from elastic metallic round wire, flat wire, wire strand and/or the like which are connected together at their distal ends 4, 5 directly 6 or by means of a connecting element 7 shown schematically in FIG. 2 and which form here a resilient bending element 8 and which are or can be connected at their proximal end 9,10 to a manipulation wire 11 which is guided inside a tube or catheter 12 and is used to pull the snare 1 into and push the snare 1 out of the catheter 12 and which can also be used as a conductor for the RF current required for the RF-surgical removal of biological tissue. One of the two snare portions, here, for example, snare portion 3, is completely insulated with an electrical insulation means 13 and the other snare portion, here, for example, snare portion 2, is not electrically insulated. The electrical insulation means 13 can be, for example, a plastic tube, and particularly an electrically insulating flexible shrink tube or a plastic coating.

Figure 2A:
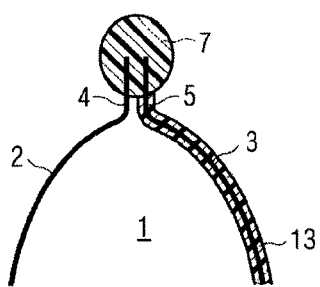
FIGS. 2a and 2b show a detail of the exemplary embodiment shown in FIG. 1.
Figure 2B:
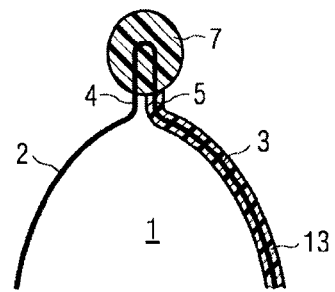

FIG. 2a shows in detail the distal end of the snare 1, the distal ends 4, 5 of the two snare portions 2, 3 being connected by a connecting element 7 which is made preferably from electrically insulating material and is preferably proof against high temperatures from electric arcing which occurs during incision. This can prevent the insulating material 13 from burning away due to electric arcing in the area of the uninsulated snare portion 2. Furthermore, this element is also intended to prevent the heat from the distal end 4 of the snare portion 2 from flowing direct into the distal end 5 of the snare portion 3 and there damaging the insulating material 13 thermally. If a sufficiently temperature-resistant material is used, the distal end of the snare can also be constructed as shown in FIG. 2b.

FIG. 3 shows an exemplary embodiment of a monopolar asymmetrically opening and closing snare 20, with which tissue to be removed can be ensnared and RF-surgically removed. This snare includes two snare portions of different length, namely, a long snare portion 21 made from resilient metallic round wire, flat wire, wire strand and/or the like and a short snare portion 22 preferably from a more flexible wire compared to the long snare portion 21. Both snare portions are connected at their distal ends 23, 24 direct 25 or, as shown schematically in FIG. 2, by means of a connecting element 7 and here form a resilient bending element 26. The long snare portion 21 is connected at its proximal end 27 to a manipulation wire 28 which is guided inside a tube or catheter 29 and is used to actively pull the long snare portion 21 into and actively push it out of the catheter 29. The short snare portion 22 can be pulled by the long snare wire 21 passively out of the catheter 29 as far as a stop 37 disposed on a stop device 35, 37 and be pulled into it or pushed by a driver 32 on a driving device 32, 33. The principle of the driving device has long been known in itself and is not essential to the embodiment. What is essential to the embodiment compared with known asymmetrical polypectomy snares, however, is that these devices are shifted into the catheter 29 in a proximal direction well away from the distal end 30 of the catheter 29, where these devices are disposed on known asymmetrical polypectomy snares and the purpose of which is described next and further down. The long snare portion 21 is preferably covered or coated along its entire length with an electrical insulation means 34. Because of the insulation layer 34 on the long snare portion 21 the outer diameter of this snare portion may be so large that it will not go through the structurally necessary narrow hole 35 in the driving device 33 without sticking. The driver 32 may at the same time also be an insulator. The short snare portion 22 is not electrically insulated.

Figure 4:
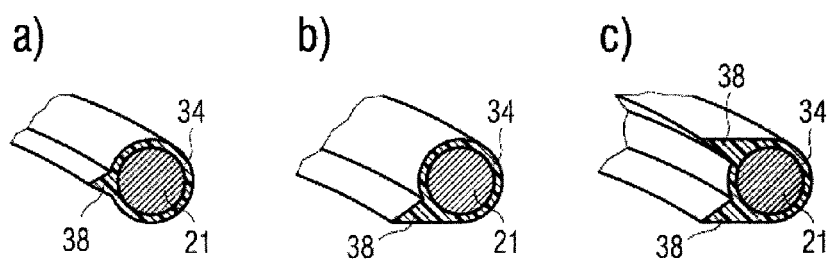
FIG. 4 shows an exemplary embodiment of the projecting portion to prevent the snare from slipping off.

FIG. 4 shows an advantageous embodiment particularly of the asymmetrical snare which is characterised in that disposed on the inner diameter of the long or RF-surgically inactive snare portion 21 is at least one more or less sharp projecting portions 38 which, on the one hand, hinders or even prevents the snare from slipping sideways off slippery mucosa and, on the other, does not or do not hinder or even prevent the snare from slipping longways off non-slippery mucosa while the snare is tightening before and during incision. This at least one projecting portion may be, for example, an integral constituent of an electrical insulation layer 34 on the long snare portion 21. The projecting portion may be designed, for example, as shown in FIG. 5 a or 5 b or 5 c. On asymmetrical snares, the long or RF-surgically inactive snare portion may during application and during incision slip only longitudinally over the tissue in and against the direction of pull. For this reason it is practical to design the surface of this snare portion so that the slide resistance is as low as possible in a longitudinal direction and as great as possible in a lateral direction.

FIG. 5 shows a further embodiment of the asymmetrical snare on which the distal area 21a of the long snare portion 21 is preshaped so that this distal area already describes a small curve before the short snare portion 22 is pulled out of the catheter 29 as far as its stop 33, 37. The non-preshaped area 21b of the long snare portion 21 is until then still located in the catheter 29.

Figure 6:
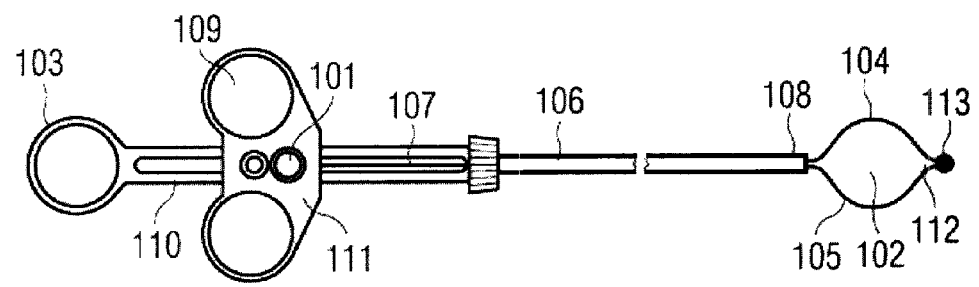
FIG. 6 shows an instrument for EPE and EMR.

FIG. 6 shows an instrument for EPE and EMR. It essentially includes an RF-surgical snare 102 having two portions 104 and 105 which are connected together by means of a direct connecting element 113 and form a resilient bending element 112. The snare can be locked with the lock 101. The instrument further includes a flexible catheter 106, at least one manipulation wires 107 which is moved in an axial direction inside the catheter to push the snare out of and pull it into the distal end 108 of the catheter 106 and to conduct the RF current required for the RF-surgical removal of the tissue around which the snare is looped and a handle 109 at the proximal end of the catheter which consists of a slide rail 110 and a sliding member 111 for manually pushing the snares out of and pushing them into the distal end of the catheter. Disposed on the sliding member is at least one electrical contacts for connecting an RF-surgical generator (RF generator).

It will be appreciated to those skilled in the art having the benefit of this disclosure that this invention is believed to provide monopolar symmetrical and monopolar asymmetrical polypectomy snares and RF-surgical snares for the endoscopically monitored separation of pathological tissue. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 1 symmetrical snare
2 snare portion of a symmetrical snare
3 snare portion of a symmetrical snare
4 distal end of the symmetrical snare
5 distal end of the symmetrical snare
6 direct connection of the distal ends of the symmetrical snare
7 connecting element
8 resilient bending element
9 proximal end of the symmetrical snare
10 proximal end of the symmetrical snare
11 manipulation wire of the symmetrical snare
12 catheter of the symmetrical snare
13 electrical insulation
20 asymmetrical snare
21 long snare portion
21a distal area of the long snare portion
21b proximal area of the long snare portion
22 short snare portion
23 distal end of the long snare portion
24 distal end of the short snare portion
25 direct connection of the long to the short snare portion
26 resilient bending element
27 proximal end of the long snare portion
28 manipulation wire of the asymmetrical snare
29 catheter of the asymmetrical snare
30 distal end of the catheter of the asymmetrical snare
31 proximal end of the insulation layer (34)
32 element of the driving device (32, 33)
33 element of the driving device (32, 33) and the stop device (33, 37)
34 insulation layer of the long snare portion of the asymmetrical snare
35 hole in the element (33) of the driving device (32, 33)
36 proximal end of the short snare portion (22)
37 element of the stop device (33, 37)
38 projecting portion
101 lock
102 RF-surgical snare
103 proximal end
104 snare portion of a symmetrical snare
105 snare portion of a symmetrical snare
106 flexible catheter
107 flexible manipulation wire
108 distal end
109 handle
110 slide rail
111 sliding member
112 resilient bending element
113 direct connection of the distal ends of the symmetrical snare

The invention claimed is:

1. A monopolar snare comprising:
a first snare portion defined by an electrical conductor that has a first length, a first proximal end, and a first distal end, said first snare portion being devoid of electrical insulation between the first proximal end and the first distal end;
a second snare portion defined by a wire having a second length, a second proximal end, and a second distal end, said second portion having an electrical insulation element covering said wire between said second distal end and said second proximal end, said second length being longer than the first length;
a catheter having an open end;
a manipulation wire guided within the catheter, said manipulation wire being either connected to the second proximal end of the second snare portion or being one piece with said second snare portion;
a first stopper immovably affixed to the catheter inside thereof and having a first opening therethrough;
a second stopper, having an outer diameter larger than a first diameter of the first opening, said second stopper being configured to slide within the catheter and being proximal to the first stopper, the second stopper having a second opening therethrough, said second opening having a second diameter, said manipulation wire passing through the second opening,
wherein said first proximal end is affixed to the second stopper;
a third stopper having an outer dimension and immovably affixed to said manipulation wire between the second proximal end and the second stopper,
wherein said outer dimension is smaller than the first diameter to effectuate passing of the third stopper through said first opening in response to the second proximal end being pulled by the manipulation wire through the catheter away from the open end;
wherein said outer dimension is larger than the second diameter dimension to prevent the third stopper from passing through said second opening in response to the second proximal end being pulled by the manipulation wire through the catheter away from the open end; and
wherein the first and second distal ends of the first and second snare portions are affixed to one another to form a distal connection portion of said snare.

2. A monopolar snare according to claim 1, wherein said distal connecting portion is defined by said first and second distal ends being electrically disconnected from one another and an electrically insulated material affixedly embedding said first and second distal ends.

3. A monopolar snare according to claim 2, wherein the electrical conductor has a first bend near the first distal end and the wire has a second bend near the second distal end.

4. A monopolar snare according to claim 1, wherein at said distal connection portion said wire and said electrical conductor are electrically connected to one another to form a longitudinally-uninterrupted unit, said distal connection portion having three spatial bends when the monopolar snare is open.

5. A monopolar snare according to claim 1, wherein said electrical insulation element contains at least one ledge defined along a length of the electrical insulation element along a length thereof.

6. A monopolar snare according to claim 1, wherein the second snare portion is configured to be characterized by at least one of (i) flexural stiffness that is higher than that of the first snare portion, and (ii) tortional rigidity that is larger than that of the first snare portion.

7. A monopolar snare according to claim 1, configured as a polypectomy snare, wherein a surface of the second snare portion contains a texture increasing friction between said snare and tissue with which said surface is brought in contact.

8. A monopolar snare according to claim 7, wherein said surface is an outer surface of the electrical insulation element.

9. A monopolar snare according to claim 1, wherein said electrical insulation element contains at least one ledge defined along a length of the electrical insulation element along a length thereof on an inner side of the symmetrical loop.

10. A radio-frequency (RF) surgical instrument comprising a monopolar snare according to claim 1, a handle operably affixed at an end of the catheter opposite to the open end, said handle having a rail and a sliding member in mechanical communication with the second proximal end and configured to be slidingly moveable along said rail.

* * * * *